(12) United States Patent
Furiki et al.

(10) Patent No.: US 7,081,625 B2
(45) Date of Patent: Jul. 25, 2006

(54) CHARGED PARTICLE BEAM APPARATUS

(75) Inventors: Masanari Furiki, Suita (JP); Kouichi Kurosawa, Hitachi (JP); Takehiko Konno, Mito (JP); Ryuichi Funatsu, Hitachinaka (JP)

(73) Assignees: Hitachi High-Technologies Corporation (JP); Hitachi Science Systems, Ltd. (JP)

( * ) Notice: Subject to any disclaimer, the term of this patent is extended or adjusted under 35 U.S.C. 154(b) by 0 days.

(21) Appl. No.: 10/700,525

(22) Filed: Nov. 5, 2003

(65) Prior Publication Data

US 2004/0129879 A1  Jul. 8, 2004

(30) Foreign Application Priority Data

Nov. 6, 2002  (JP) .............................. 2002-321958

(51) Int. Cl.
G01N 23/00 (2006.01)
G21K 7/00 (2006.01)
G01R 31/305 (2006.01)
G01R 31/25 (2006.01)

(52) U.S. Cl. .................. 250/310; 250/306; 250/307; 250/309; 324/751

(58) Field of Classification Search ................ 250/306, 250/307, 309, 310; 324/751, 765
See application file for complete search history.

(56) References Cited

U.S. PATENT DOCUMENTS

| | | | |
|---|---|---|---|
| 6,388,747 B1 * | 5/2002 | Nara et al. | 356/394 |
| 6,476,913 B1 * | 11/2002 | Machida et al. | 356/394 |
| 6,566,654 B1 * | 5/2003 | Funatsu et al. | 250/310 |
| 6,618,850 B1 * | 9/2003 | Nishiyama et al. | 716/20 |
| 6,700,122 B1 * | 3/2004 | Matsui et al. | 250/310 |
| 6,855,929 B1 * | 2/2005 | Kimba et al. | 250/310 |
| 2001/0019411 A1 * | 9/2001 | Nara et al. | 356/394 |
| 2002/0028399 A1 * | 3/2002 | Nakasuji et al. | 430/30 |
| 2004/0129879 A1 * | 7/2004 | Furiki et al. | 250/310 |
| 2005/0121611 A1 * | 6/2005 | Kimba et al. | 250/311 |
| 2005/0194536 A1 * | 9/2005 | Furiki et al. | 250/311 |

FOREIGN PATENT DOCUMENTS

| | | | |
|---|---|---|---|
| JP | 2001 127125 | * | 5/2001 |
| JP | 2002-124555 | | 4/2002 |

OTHER PUBLICATIONS

Kurosawa, et al., Establishment of the high throughput analysis method of the internal defect in a semiconductor device., pp. 7-12 (2002), Japan.

* cited by examiner

*Primary Examiner*—Nikita Wells
*Assistant Examiner*—Bernard E. Souw
(74) *Attorney, Agent, or Firm*—Dickstein Shapiro Morin & Oshinsky LLP

(57) ABSTRACT

The object of the present invention is to transmit the position information of a defect that has been specified by means of a circuit pattern inspection apparatus quickly and precisely so that the position information is efficiently used in another apparatus. Marking is carried out on the peripheral area of the defect by use of a charged particle beam irradiation mechanism of the inspection apparatus. The marking realizes sharing of the defect position information with another apparatus. The marking technique includes deposition of a deposit and charging up by means of irradiation of a charged particle beam. The marking in the inspection apparatus allows the defect position information to be transmitted to another apparatus more correctly and easily, and as a result, analysis accuracy is improved and analysis time is shortened.

6 Claims, 12 Drawing Sheets

RESIDUAL OXIDE FILM OR RESIST CANNOT BE CONFIRMED
FROM SAMPLE SURFACE

DEFECT

CHARGED PARTICLE BEAM APPARATUS

BACKGROUND OF THE INVENTION

1. Field of the Invention

This invention relates to a technique suitable for sample analysis of semiconductor devices in which it is difficult to analyze the defect in depth from the surface.

2. Description of Related Art

Higher circuit density has been required with progress of higher circuit integration of devices. Actually, defect inspection apparatus for inspecting semiconductor devices is required to analyze not only the defect information on the surface but also the defect/foreign-particle information in the internal of a sample.

For such analysis, the analysis of defect/foreign-particle on the surface and analysis of cross-section image for analyzing internal defect/foreign-particle are carried out on the positional information obtained by means of an inspection apparatus by use of a focused ion beam apparatus (FIB), scanning electron microscope (SEM), and transmission electron microscope (TEM).

For example, in the case of SEM, non-contact defect, disconnection of the wiring, and short circuit of the wiring in the internal of a semiconductor sample can be detected based on the contrast (voltage contrast) due to charging effect of an electron beam irradiation. This technique is disclosed in, for example, JP-A No. 124555/2000.

SUMMARY OF THE INVENTION

However, measurement of the contrast due to charging is insufficient for higher precision analysis. It is desirable that the cross section of defect is observed by use of a FIB apparatus after the defect is checked on the voltage contrast image, but this technique is problematic as described herein below.

For example, when a defect point is specified by use of a SEM on a sample on which many similar bit patterns are arranged, it is difficult to specify the point by use of a FIB apparatus.

The present invention has been accomplished to solve the above-mentioned problem, and the object of the present invention is to provide a technique, apparatus, and system that is suitable for easily specifying a defect by use of a lower analytical apparatus after the defect has been checked by use of an SEM.

To accomplish the above-mentioned object, the present invention provides a technique for forming an image in which a charged particle beam is scanned on a sample to form an image of the scanned area, wherein the charged particle beam is irradiated selectively onto a specified portion so as to cause charging on the specified portion that is different from charging of the scanned area other than the specified portion or so as to form a carbon-base deposit on the specified portion.

The other structures and detailed structures of the present invention will be described in the section of "detailed description of the preferred embodiments."

BRIEF DESCRIPTION OF THE DRAWINGS

Preferred embodiments of the present invention will be described in detail based on the followings, wherein.

DETAILED DESCRIPTION OF THE PREFERRED EMBODIMENTS

The embodiment of the present invention describes an analysis technique and a system used for applying the analysis technique to analyze the electrical defect quickly, easily, and precisely in the internal of a semiconductor device in which it is difficult to found out and analyze an electrical defect by means of the conventional apparatus, wherein the system comprises a scanning electron microscope (referred to as SEM hereinafter) that functions as an inspection apparatus for finding out the electrical defect in the internal of a semiconductor device particularly that is difficult to be found by means of other apparatus or the defect on the sample surface differently from other charged particle beam apparatus, and comprises an FIB or electron microscope for analyzing the electric defect more in detail that has been found by means of the above-mentioned inspection apparatus.

An electron beam inspection system can sensitively detect an electrical defect (voltage contrast) such as non-contact defect, disconnection of the wiring, and short circuit of the wiring in the internal of a semiconductor sample. However, these detected electrical defect can rarely be analyzed by means of observation of the semiconductor sample surface.

Figure 1:
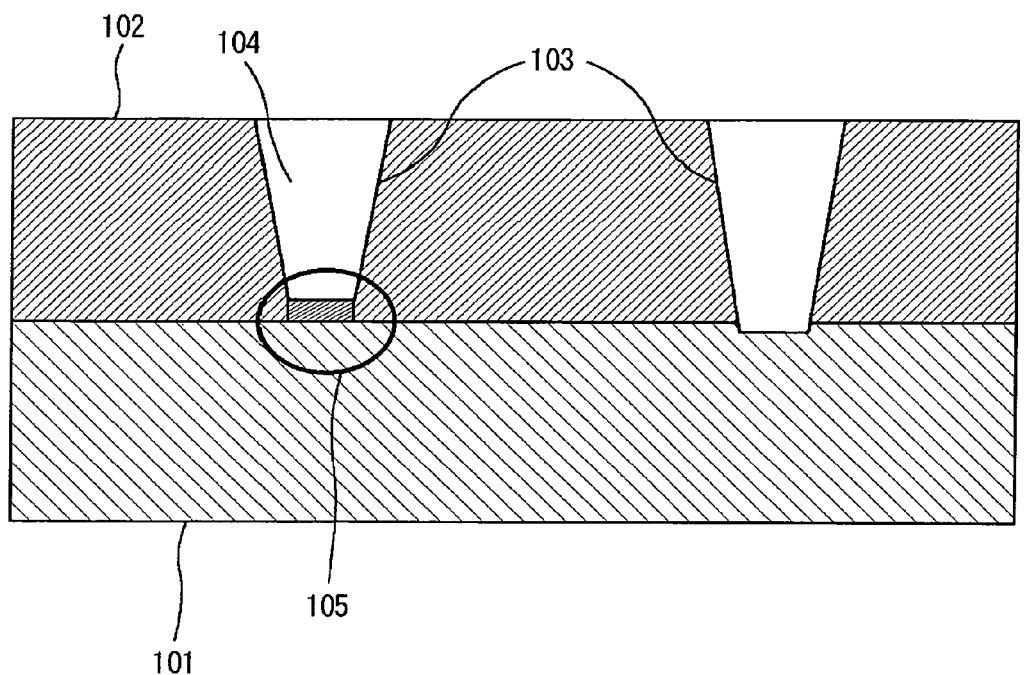
FIG. 1 is a schematic diagram showing an exemplary electrical defect in the internal of a sample that is detected by use of a SEM inspection apparatus.

An exemplary detected defect is shown in FIG. 1. The sample comprises a Si substrate 101, an oxide film 102, and contact holes 103 in which conductive material 104 is embedded. A defect 105 that is a residual thin film of oxide film or resist (etching residue of oxide film or resist) formed between the Si substrate and conductive material 104 due to insufficient etching. It is difficult to find out such defect by means of surface observation.

As described hereinabove it is difficult to find out an electrical defect such as non-contact defect, disconnection of the wiring, and short circuit of the wiring that are formed in holing process of a semiconductor device by means of observation of the sample surface, but the SEM inspection apparatus 216 can sensitively detect such a defect based on the voltage contrast.

In the case of this exemplary defect, secondary electrons are supplied from normal portion of the substrate (etching is normal and conduction between the conductive material embedded in a contact hole and the substrate is normal) to result in low charging voltage of the sample surface.

On the other hand, the resistance between the abnormal portion of the substrate and the conductive material is high (there is residual non-conductive material such as oxide film on the bottom of the contact hole and non-conduction is resulted between the embedded conductive material and the substrate because of insufficient etching), and electrons are not supplied from the substrate. As a result, the charging voltage of the sample surface on the abnormal portion is higher than that on the normal portion. The high charging voltage of the sample surface causes drawing back of low energy secondary electrons to the sample surface because of potential barrier arising from charging on the sample surface, and the abnormal portion is detected in the form of a dark defect.

Then, a cross section of the detected defect is formed by use of a FIB, and the cross section is observed by use of an observation apparatus such as an electron microscope at high resolution desirably.

A technique employed in the present embodiment is described with reference to a flow chart shown in FIG. 2 in comparison with another analysis technique. FIG. 3 shows an exemplary defect position information acquired in accordance with another analysis technique.

In technique A, the pattern position 305 having thereon a defect to be analyzed (pattern having a defective bit thereon) is specified from among the inspection sample 301 (chip) based on the detected defective bit pattern position information in the inspection apparatus used for inspection in step 201. Next, an operator counts the number of patterns from the pattern corner to the defective bit pattern 303 to obtain the defective bit pattern position information 304 as shown in the enlarged diagram 302 (step 203). Next, the sample is moved to an FIB apparatus 217 to carry out cross section forming or sample slicing (step 204).

The inspection sample 301 that has been set in the FIB apparatus 217 is observed by means of image observation function of the FIB apparatus 217 to thereby find out the pattern position 305 on which the defect is located (step 206).

Next, the operator counts, based on the defective bit pattern position information 304, the number of the patterns from the corner that is the reference point for the found pattern to thereby specify the defective bit pattern 303 (step 206), and this step is followed by FIB/cross section forming (step 214) and cross section observation (step 215) for analysis.

The above-mentioned technique is involved in the problem as described herein below. A chip of semiconductor sample includes the same bit patterns of several hundreds or more in many cases, and when cross section working of the defective bit pattern, that is an electrical defect, is carried out for the chip, the inspection apparatus operator transmits the position information to the FIB apparatus based on the electrical defect position information that has been obtained by means of the inspection apparatus.

For example, the operator counts the number of patterns from the corner of the pattern up to the defect position by means of the inspection apparatus at first, and then the FIB operator counts the number of the patterns from the pattern corner similarly in the FIB or confirms the defective pattern position by means of coordinate linkage for cross section working.

In this technique, it is difficult to obtain the correct defective bit pattern position information 304 because the operator of the SEM inspection apparatus 216 and the operator of the FIB apparatus 217 can miscount the number of patterns. For example, an operator can mistake the defective bit pattern 302 for the neighboring bit pattern.

Furthermore, in addition to the correctness deterioration of the position information due to the operator, the image information obtained by means of the SEM inspection apparatus 216 and FIB apparatus 217 includes image strain and length scale error, which makes it difficult to specify the correct defective bit pattern position based on only the coordinate data. Thus, these apparatus themselves have causes for correctness deterioration.

Searching of the pattern position 305 having a defect thereon and specifying of the defective bit pattern 303 based on the counting of the number of patterns carried out by the operator require much working and long time for analysis. Particularly, it is relatively easy to search a defect to be analyzed if the defect is located near the pattern corner or specific point, but it takes a long time to specify the defective pattern if the defect is located near the center because the number of patterns to be counted is large. Furthermore, damage of the sample surface becomes serious due to prolonged FIB observation.

In technique B, even when the defective bit pattern 303 to be analyzed is observed by means of another reviewing apparatus at higher resolution, the same problem as encountered in the above-mentioned technique A occurs because an operator has to count the number of patterns to obtain the defective bit pattern position information 304. Furthermore, another reviewing apparatus can mis-detect the defect, and the technique described hereinabove is not effective.

As described hereinabove, the coordinate linkage technique between the inspection apparatus and the observation apparatus such as FIB and other observation apparatus has not been established, and as a result, the cross section analysis currently requires a long time. Probability of miscount is large, and the miscount results in deterioration in correctness. To avoid the problem the patterns are marked at certain intervals in FIB observation, but long analysis time cannot be avoided and also deterioration in correctness cannot be avoided.

In the above-mentioned conventional technique, it has been difficult to find out the electrical defect in the internal of the sample and the defect on the sample surface that have been detected using an SEM inspection apparatus, stably and without damage by means of surface observation using FIB and the like. As a result, correctness of the defect position information transmitted is deteriorated and the analysis takes a long time.

The present invention provides a technique and system in which an SEM inspection apparatus capable of sensitively detecting the electrical defect marks the defects precisely, quickly and simply based on the defect position information obtained in inspection, and another apparatus utilizes the markings to analyze the defects, thereby improving the correctness of the position information transmitted in the analysis and shortening the analysis time. Thus, the present invention is effective to solve the above-mentioned problem.

According to the present invention, a system comprises a circuit pattern inspection apparatus that irradiates a charged electron beam onto a plurality of areas of a circuit pattern, detects secondary electron particles generated from the circuit pattern to form images of the irradiated areas, and compares the images of the plurality of areas to detect the defect/foreign-particle of the circuit, an inspection apparatus (for example, first charged particle beam apparatus) that is capable of finding out the electrical defect caused from electrical failure in the internal of the sample that has been found by means of the inspection apparatus, in which it is difficult to find an electrical defect by means of other apparatus, and capable of finding out the defect formed on the sample surface, a charged particle optical system that focuses the charged particle beam released from the charged particle beam source and scans the focused charged particle beam on the sample, and a detection means that detects the secondary signal particles generated from the sample when the charged particle beam is scanned. The present invention proposes a technique for marking in the inspection apparatus that improves the transmission correctness of defect position information to be analyzed between the charged particle beam apparatus for obtaining the sample image based on the secondary signal particle detection means and the charged particle beam apparatus for working on the area irradiated with the charged particle beam by means of irradiation of the charged particle beam onto the sample in addition to the above-mentioned function, and that shortens the analysis time thereby.

The present invention provides a system and marking technique in which the sample stage is moved precisely based on the electrical defect information obtained by means of inspection, and the charged particle beam that is used for inspection or that is different in irradiation condition is irradiated onto the periphery of the electrical defect and scanned in X and Y directions for marking in the inspection apparatus that is capable of finding out the electrical defect precisely that is difficult to be found out by means of the lower analysis apparatus (for example, secondary charged particle beam apparatus).

Furthermore as the technique for marking in the inspection apparatus, the present invention provides a marking technique and a system used for applying the marking technique in which gas is introduced onto the area irradiated with the charged particle beam to thereby significantly increase the amount of deposit on the sample surface and to thereby widen the area that is irradiated with the charged particle beam, and as a result, the wider area is marked. Furthermore, the present invention provides a marking technique and a system used for applying the marking technique which utilizes the phenomenon that gas is not deposited only on the area that is irradiated with the charged particle beam when the gas is sprayed onto the cooled sample surface to form gas deposit on the sample surface.

Furthermore, the present invention provides a marking technique and a system used for applying the marking technique in which unordinal contrast (charge up) due to charging phenomenon is caused on the area irradiated with the charged particle beam by means of charged particle beam irradiation.

According to the above-mentioned marking techniques, the defect position to be analyzed can be searched at higher precision between apparatuses having no position information joint ownership function or between apparatuses having no sample stage and no sample holder. The analysis time is shortened and the analysis is carried out easily.

Figure 10:
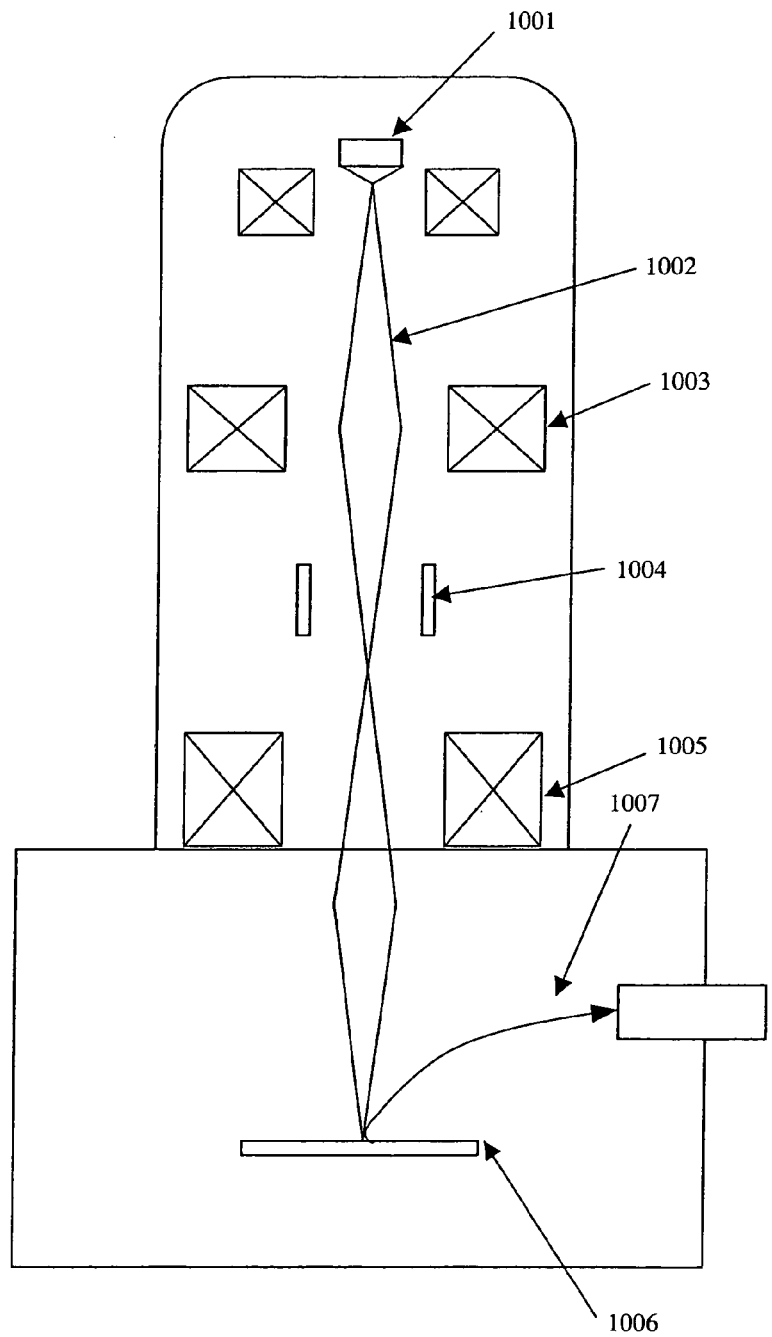
FIG. 10 is a schematic structural diagram of a SEM.

The observation/analysis system used in the present embodiment is described hereinafter with reference to FIG. 10 to FIG. 12. FIG. 10 is a schematic structural diagram of an SEM described in the present embodiment. An electron beam 1002 released from an electron gun 1001 is irradiated onto a sample 1006 through a condenser lens 1003 and an objective lens 1005. The electron beam 1002 is scanned one-dimensionally or two-dimensionally on the sample 1006 by a scan deflector 1004. A detector detects electrons (secondary electrons and reflected electrons) released from the sample 1006 with scanning of the electron beam 1002, and the detection signal is arranged one-dimensionally or two-dimensionally synchronously with the deflection signal that is supplied to the scanning deflector 1004 to thereby form, for example, an image. The image formed as described hereinabove is displayed on, for example, a sample image display unit that is not shown in FIG. 10. The image may be formed based on the absorption current that is absorbed by the sample.

The SEM shown in FIG. 10 has a sample stage for changing the sample position and an image shift deflector for changing the scanning range position of the scanning deflector 1004 (not shown in FIG. 10). The sample stage and image shift deflector are positioned based on the position information of the sample defect obtained from the upper inspection apparatus (SEM defect detection apparatus) by means of a control unit not shown in FIG. 10 so that the scanning rage covers the place near the defect or defect itself.

An energy filter may be provided between the electron detector and the sample to grasp the charging of the sample more correctly. The energy filter functions to discriminate electrons depending on the energy of the electrons released from the sample. The energy of the electrons released from the charged portion is different from that of the electrons released from the portion other than the charged portion depending on the charge voltage. The energy-discriminated electrons effectively make the contrast between charged portion and non-charged portion distinct, enabling it to discriminate the charged portion more distinctly.

Figure 11:
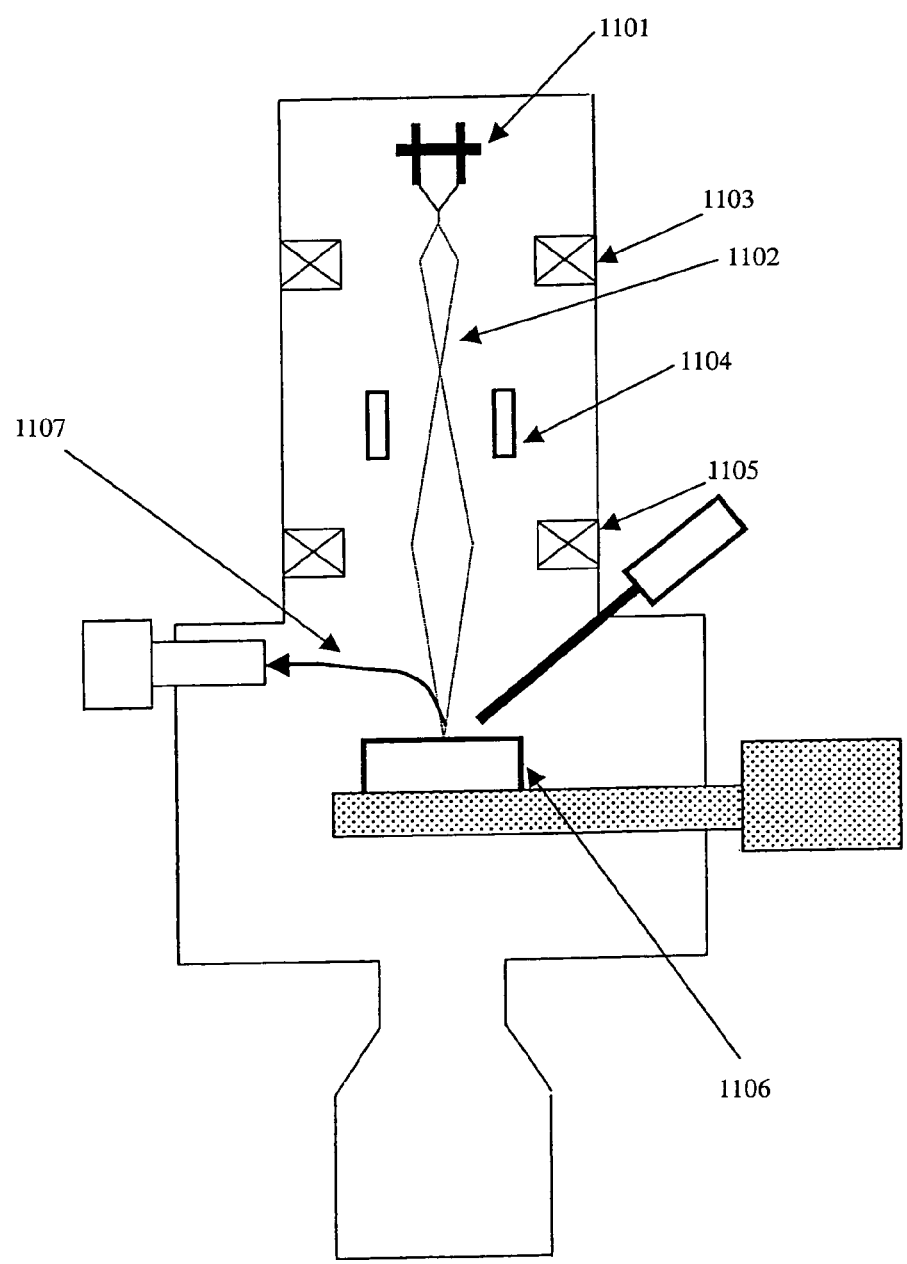
FIG. 11 is a schematic structural diagram of a FIB.

FIG. 11 is a schematic structural diagram of an FIB according to the present embodiment. An ion beam 1102 released from an ion source 1101 is focused through the condenser lens 1103 and objective lens 1105, and irradiated onto a sample 1106. A scanning deflector 1104 scans the ion beam 1102 on the sample 1106.

The detector detects secondary electrons and secondary ions released from the sample 1006 with scanning of the ion beam 1102, and the detection signal is arranged one-dimensionally or two-dimensionally synchronously with the deflection signal that is supplied to the scanning deflector 1104 to thereby form, for example, an image. The image formed as described hereinabove is displayed on, for example, a sample image display unit that is not shown in FIG. 11. The FIB shown in FIG. 11 has a sample stage and image shift deflector, and the scanning position is controlled by means of a control unit that is not shown in FIG. 11 similarly to the SEM described with reference to FIG. 10.

Figure 12:
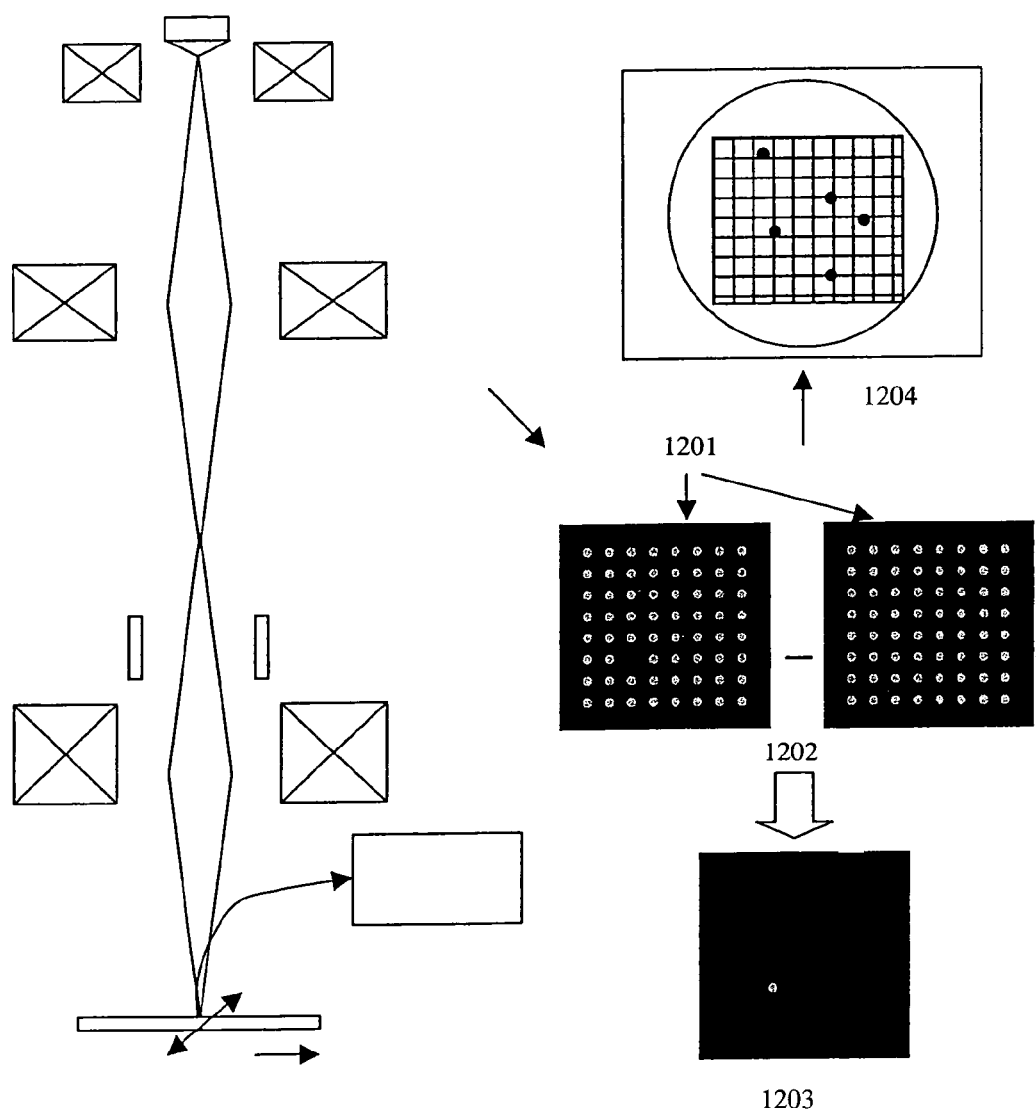
FIG. 12 is a schematic structural diagram of a SEM defect inspection apparatus.

FIG. 12 is a schematic diagram of an SEM defect inspection apparatus (circuit pattern inspection apparatus) according to the present embodiment. The SEM defect inspection apparatus is an apparatus for forming an image operated in the same principle as that of the SEM described with reference to FIG. 10. The SEM defect inspection apparatus irradiates (scans) an electron beam on the area that includes a defect or the peripheral area of the defect on the circuit pattern to thereby image the defect in the scanned area.

The SEM defect inspection apparatus is an apparatus that compares two or more images obtained at the same address of two chips that are adjacent each other on, for example, a semiconductor wafer to thereby specify the defect. In detail, the SEM defect inspection apparatus obtains an image 1201 at the same address of two different chips, carries out image comparison processing 1202, and carries out circuit defect detection 1203. The position information of the detected defect is stored in a memory apparatus that is not shown in FIG. 12. The position information may be displayed in the form of a defect map 1204. A control unit controls the operation described hereinabove. Not only the defect but also, for example, foreign particle is detected by comparing two images as long as the foreign particle is a matter that is specified based on the difference between two images.

The SEM and FIB described with reference to FIG. 10 and FIG. 11 respectively are used to observe or analyze the defect that is detected by means of the SEM defect inspection apparatus. To specify the defect position, the SEM defect inspection apparatus detects the defect position, and the sample stage and image shift deflector of the SEM and FIB are controlled based on the position information. The defect position information may be transmitted from the SEM defect inspection apparatus to the SEM and FIB through a network. Otherwise the defect position information may be stored in the memory medium of the SEM defect inspection apparatus, and the stored defect position information is used for positioning in the SEM and FIB.

Figure 2:
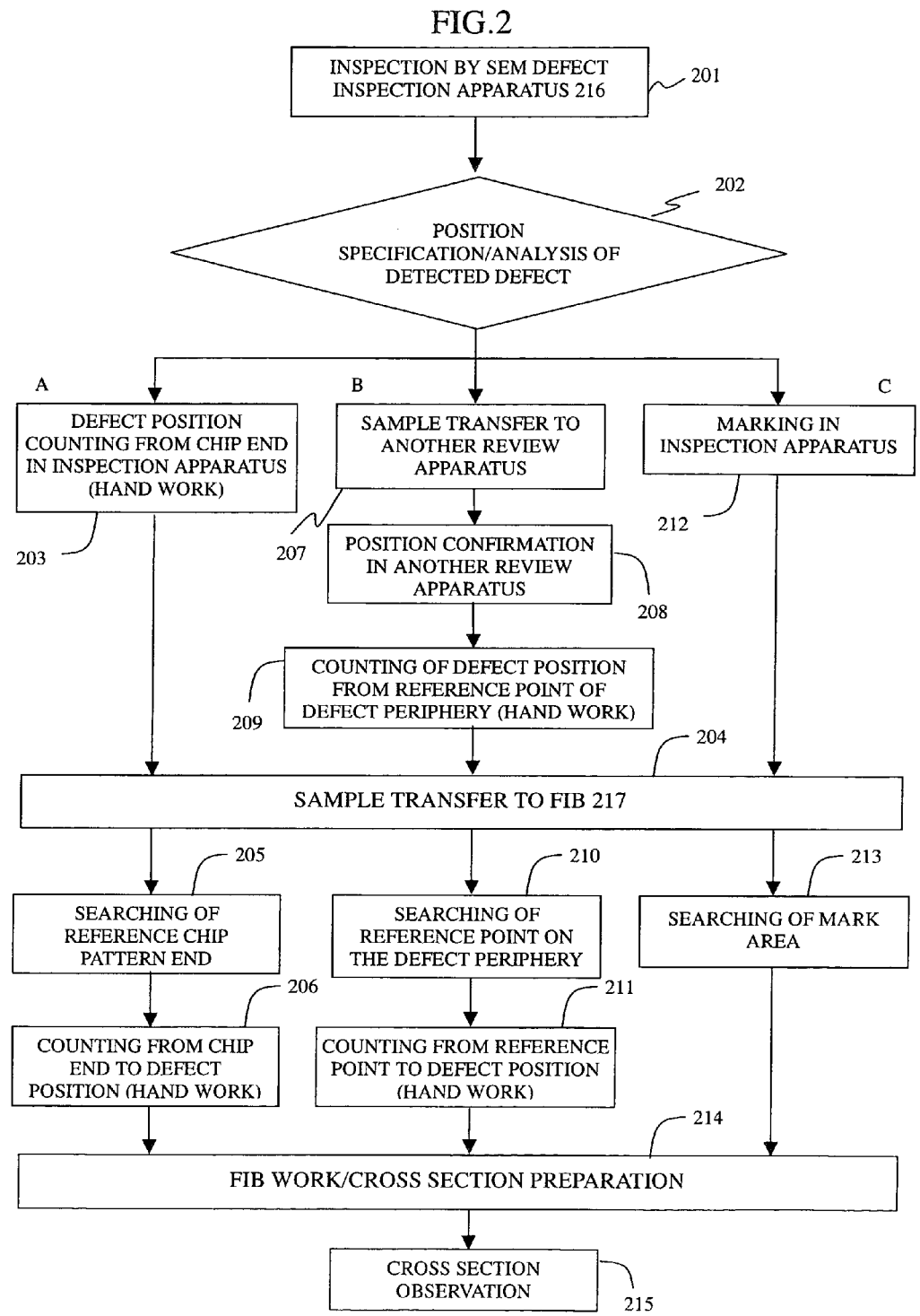
FIG. 2 is a flow showing the defect analysis technique to be applied on a semiconductor sample.
Figure 3:
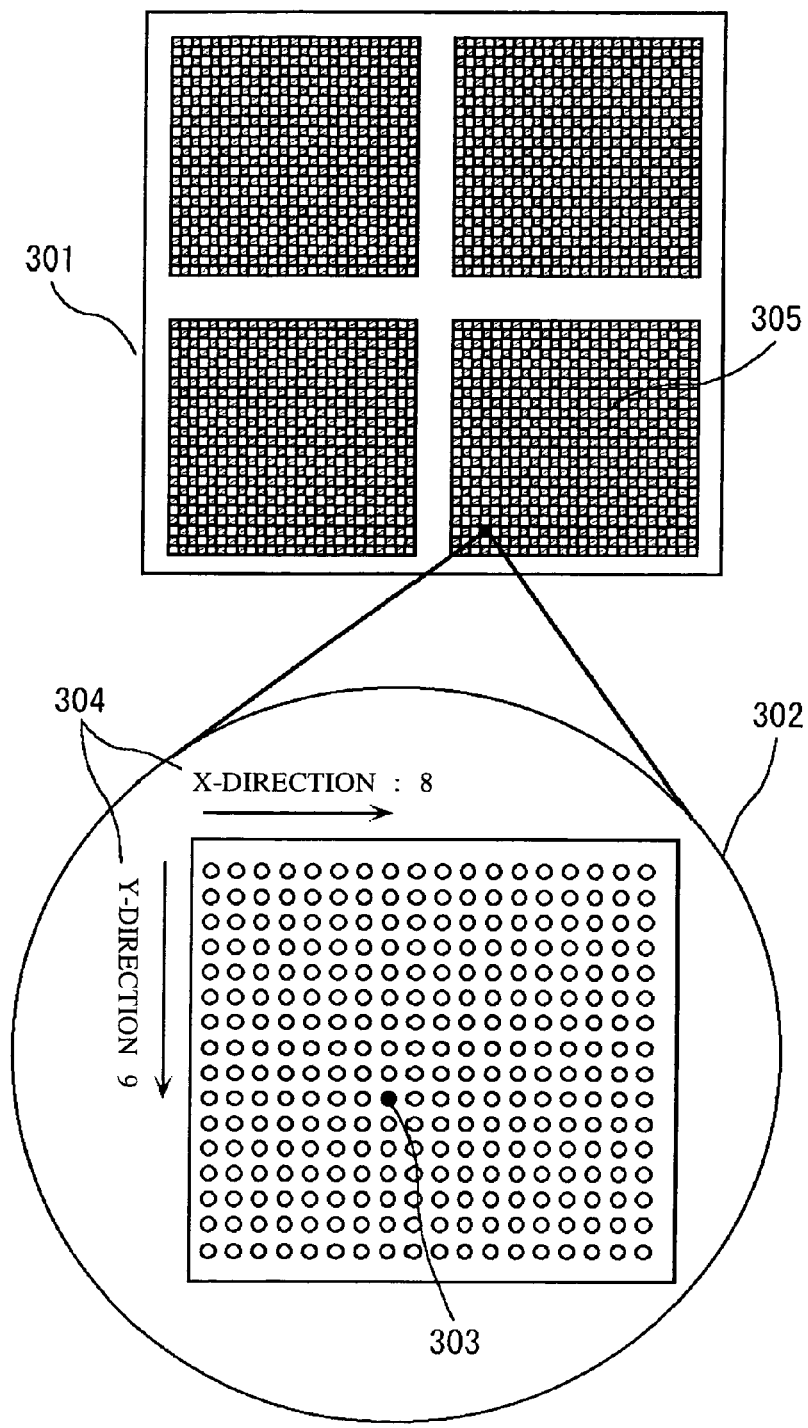
FIG. 3 is a schematic diagram showing an exemplary defect position information acquisition.
Figure 4:
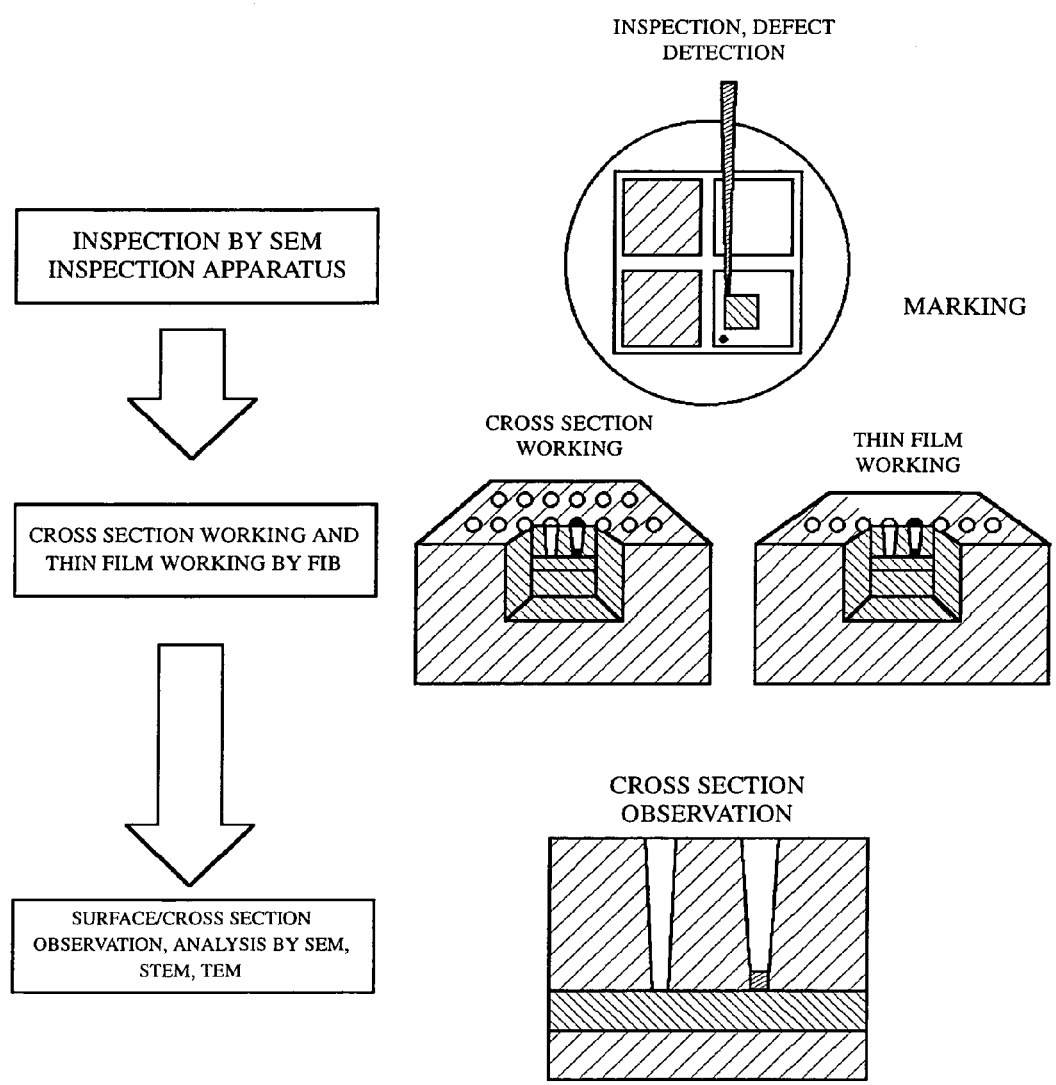
FIG. 4 is a schematic diagram showing the structure of a new defect analysis technique system to be applied on a semiconductor sample.

The analysis process of the defect addressed in the present embodiment is shown in C of the flow chart of FIG. 2. FIG. 4 shows an exemplary system structure of the present invention. At first, the defect of the circuit of the inspection sample 301 is inspected by use of the SEM inspection apparatus 216 (step 201).

In the inspection, a charged particle beam is irradiated onto a plurality of areas of the circuit pattern, secondary charged particles generated from the circuit pattern is detected to form an image of the irradiated area, and images of the plurality of areas are compared to thereby detect defect/foreign-particle of the circuit. Next, the position of the defect detected in the inspection step 201 is specified/analyzed (step 202).

The position information of the detected defective bit pattern 303 is stored automatically in the apparatus, and transferred to the position of the defective bit pattern 303 to be analyzed by use of a highly accurate stage with a laser interferometer in the SEM inspection apparatus 216 that is used for the defect detection inspection.

Next, the periphery of the defective bit pattern 303 is marked by means of electron irradiation function of the SEM inspection apparatus 216 (step 212). It is possible to simultaneously specify the position information of the pattern position 305 on which the defective bit pattern is located and the position of the chip 301 on which the pattern position 305 is located by use of the mark.

In the marking process, the electron beam is irradiated on specified portions to be marked on the image formed by means of electron beam scanning in the SEM inspection apparatus so that the defect is detectable by means of not only the SEM inspection apparatus but also other charged particle beam apparatus. In the selective electron beam irradiation, the specified portions are charged or covered with deposited carbon. The charge or deposited carbon remains on the sample after the sample is taken out from the SEM inspection apparatus.

Next, the sample is transferred to the FIB apparatus 217 to prepare cross section or slice the sample (step 204). The inspection sample 301 set in the FIB apparatus 217 is observed by means of image observation function of the FIB apparatus 217 to search the mark (step 213) and to specify the defective bit pattern 303. The sequence proceeds to analysis process such as FIB working/cross section preparation (step 214) and cross section observation (step 215).

The marking on the periphery of the defective bit pattern 303 (step 212) allows the defective bit pattern 303 to be searched easily in the FIB apparatus 217, and as a result, the searching time is shortened significantly. Furthermore, the marking in the SEM inspection apparatus 216 that is used for inspection is effective to reduce the correctness reduction factor of the position information due to human factor and the correctness reduction factor of the position information due to inter-apparatus factor.

Figure 5:
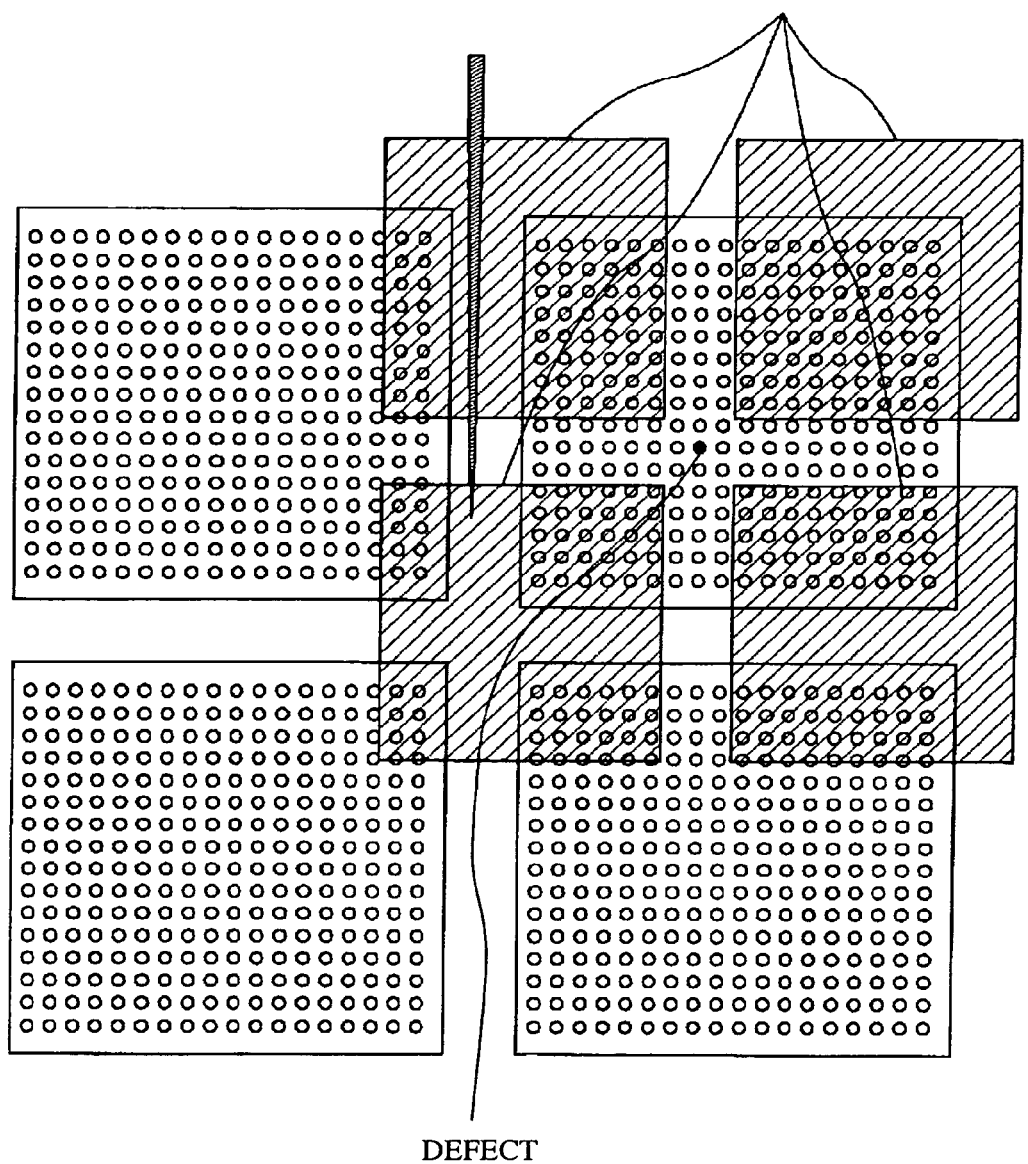
FIG. 5 is a schematic diagram showing an exemplary marking technique.

Next, marking technique is described. FIG. 5 shows an exemplary marking. Square marks 501 are formed on the periphery of the defective bit pattern 303 detected by means of the SEM inspection apparatus 216 by scanning the electron beam 502 in the directions X and Y. The square marking 501 is carried out on, for example, four peripheries of the defective bit pattern 303 to thereby specify the position of the defective bit pattern 303 to be at the center of the bit pattern of three columns and three rows surrounded by the square marks 501. The marking technique may be various, and shape of mark other than square may be employed and number of marks may be one or plural depending on the case. It is desirable that the shape of the mark is suitable for specifying the defect position correctly as described hereinabove. For example, the mark may be an arrow directed to the defect. Otherwise, when a TEM sample is prepared by use of an FIB, a mark that prescribes a cross section to be observed by means of TEM may be prepared in the SEM inspection apparatus 216. According to such technique, it is possible to carry out cross section working immediately after the sample is transferred to the FIB without marking for specifying the cross section position in the FIB.

The marking described in the present embodiment does not require holing on a sample, as is required in case of the marking by means of cutting in FIB, and therefore it is possible to form a relatively large mark for the size of the defect, as shown in FIG. 5. As a result, it is easy to search the defect in the field of view in the SEM and FIB (position setting of scanning area of the charged particle beam). The size of the mark is desirably so large as to be confirmable on an image having magnification lower than that of the image finally used for observation/analysis of the defect. Confirming of the mark in the field of view of the image with magnification lower than the final magnification effectively reduces the work required for searching in the field of view.

The control unit of the SEM defect inspection apparatus may have the function to mark so as to automatically specify the position of the defect by specifying the defect location.

The SEM and FIB desirably have a program for specifying the mark prepared in the SEM defective inspection apparatus by means of pattern matching. If the SEM defect inspection apparatus and the SEM or FIB share the mark shape information, it becomes possible to quickly observe and analyze the defect information specified in the SEM defect inspection apparatus by means of the SEM or FIB.

The pattern matching is a technique to determine correlation between the detected image and a previously-registered template, and to specify that the pattern in the image is the same as the registered template in case the correlation value is a predetermined value or larger. In the present embodiment, a template having the same shape as the mark prepared in the SEM defect inspection apparatus is registered in the SEM and FIB, and pattern matching is carried out for quick observation/analysis.

Figure 6:
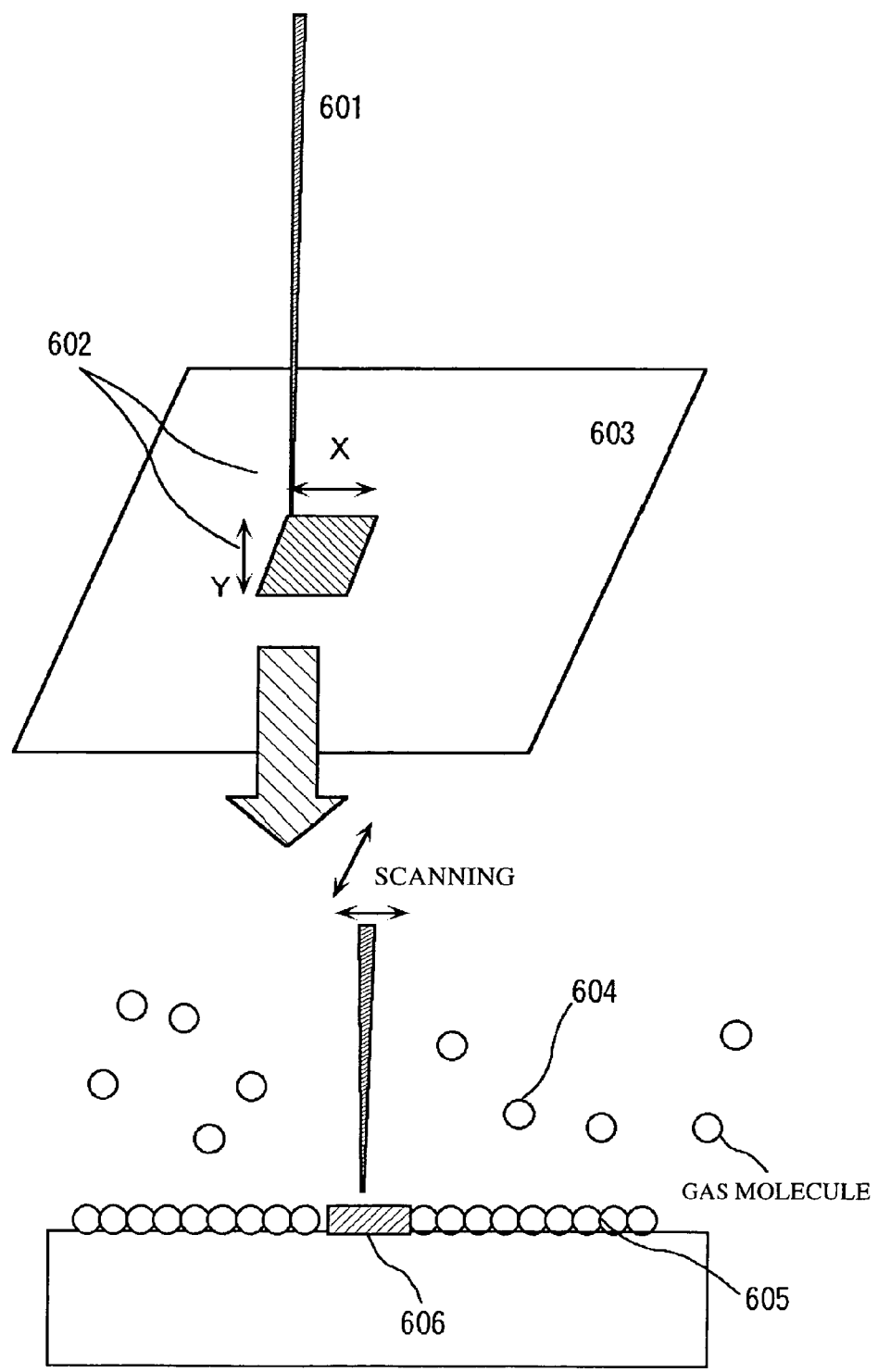
FIG. 6 is a schematic diagram showing a marking technique applying electron beam irradiation.

Next, a technique for emphasizing the contrast of the mark on a sample is described. FIG. 6 shows a marking technique in which an electron beam is used. The electron beam 601 is irradiated on the sample 603 with scanning of scanning width of X and Y 602. Residual gas 604 in the sample chamber or gas 604 generated from the sample chamber exists near the sample, and gas 605 lies on the sample. These gases interact with the electron beam 601 to form carbon-base deposit 606 on the area irradiated with the electron beam. As a result, a mark 501 is formed.

Figure 7:
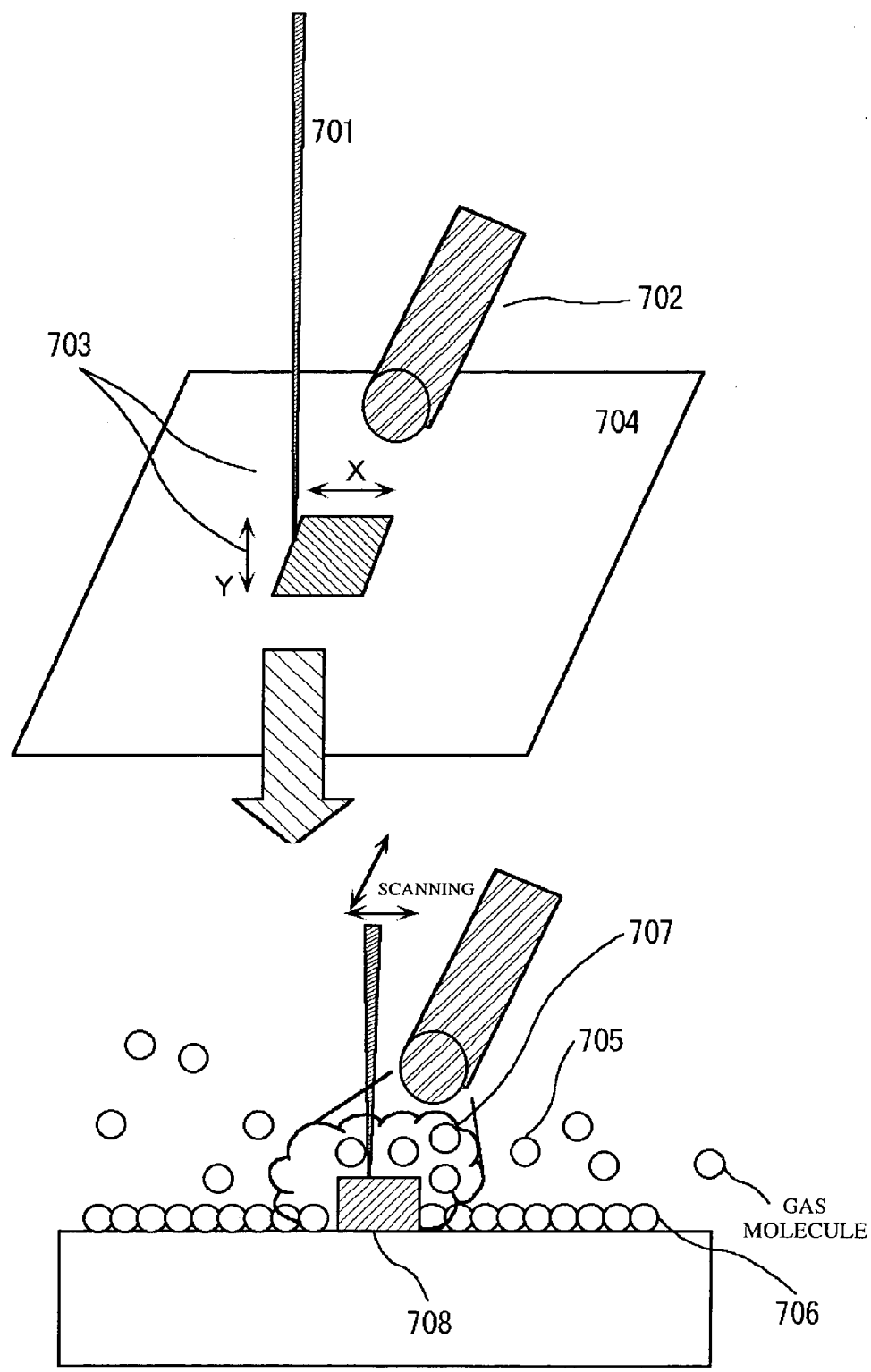
FIG. 7 is a schematic diagram showing a marking technique applying electron beam irradiation with introduction of deposition gas.

Next, FIG. 7 shows another exemplary marking technique that utilizes an electron beam irradiation and gas introduction. An electron beam 701 is irradiated onto a sample 704 with scanning of the scanning width of X and Y 703. Residual gas 705 in the sample chamber or gas 705 generated from the sample chamber exists near the sample, and gas 706 lies on the sample. In addition to these gases, carbon-base gas or tungsten-base gas 707 is sprayed from a gas introduction nozzle 702 onto a sample 704. These gases including the introduced gas interact with the electron beam 701 to form deposit 708 on the area irradiated with the electron beam. The introduction of the gas 707 onto the area irradiated with the electron beam 701 is very effective to increase the amount of the deposit 708. The wider area irradiated with the electron beam 701 brings about wider marking area.

Figure 8:
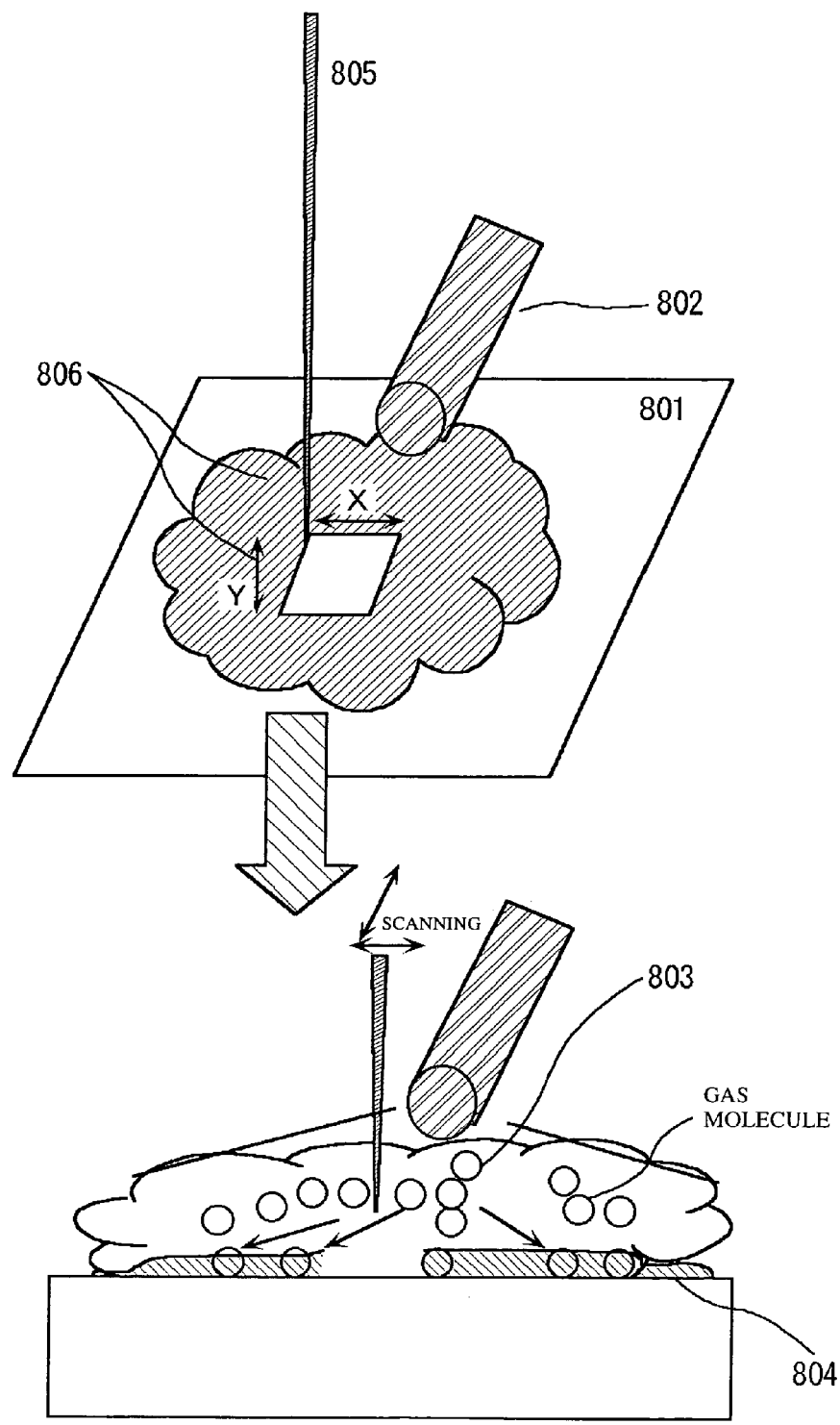
FIG. 8 is a schematic diagram showing a marking technique with spraying of deposition gas onto a cooled sample.

FIG. 8 shows another technique. Carbon-base gas 803 or tungsten-base gas 803 is sprayed from a gas introduction nozzle 802 onto a sample 801 that is cooled by means of a sample cooling mechanism. The gas is absorbed/deposited on the gas spraying area to form a deposit 804. At that time, an electron beam 805 is irradiated onto the gas spraying area with scanning of the scanning width of X and Y 806 and the temperature is kept at a temperature higher than the environmental temperature. As a result, forming of the deposit on the area irradiated with the electron beam is suppressed. The electron beam 805 is irradiated on the peripheral area of the defective bit pattern 303 to thereby mark on the sample by applying this technique.

The technique for cooling a sample includes a technique using refrigerant such as liquid nitrogen and a technique using a Peltier element.

Figure 9:
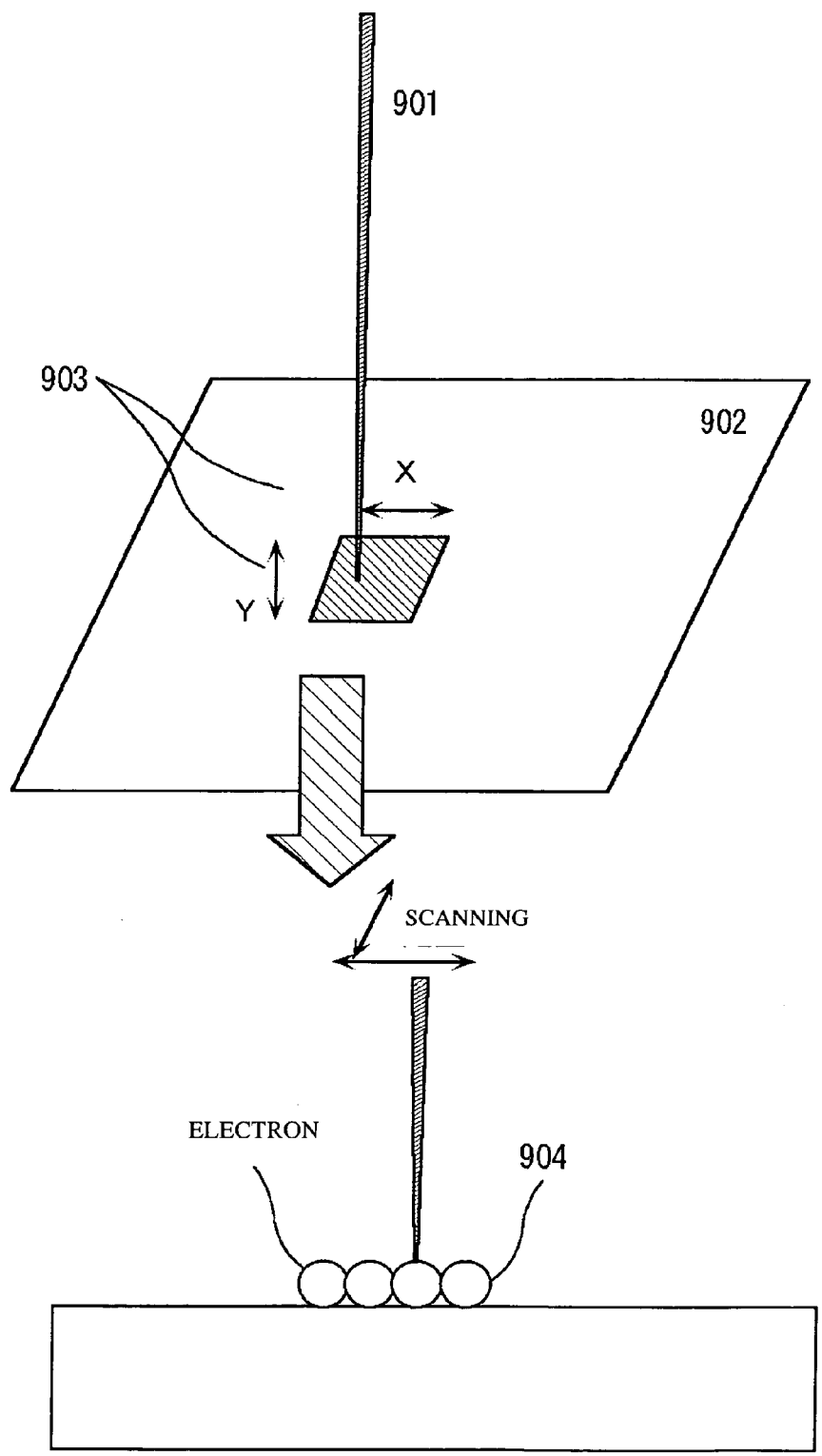
FIG. 9 is a schematic diagram showing a marking technique utilizing charge up phenomenon due to electron beam irradiation.

Next, FIG. 9 shows a marking technique without gas deposition on a sample. An electron beam 901 is irradiated onto a sample 902 with scanning of the scanning width of X and Y 903. The electron beam 901 is directed continuously on the same area on the sample to cause charge up (charging phenomenon). Unordinal contrast due to charge up can be utilized for marking.

It is desirable that marking is carried out by means of electron beam irradiation function of the SEM inspection apparatus 216. Marking is carried out without using other apparatus or without additional significant modification to the apparatus, and as a result, increase of analysis system cost is reduced. Furthermore, marking in the SEM inspection apparatus 216 consequently reduces the mistakes of bit pattern and error in the apparatus to the minimum.

In the above-mentioned marking technique, damage to a sample is reduced to the minimum, because a sample is not physically cut as is in the sputtering process using an ion beam.

In the present embodiment, the exemplary observation/analysis technique in which marking is carried out in an SEM defect inspection apparatus and the defect that is specified with the mark is observed/analyzed by means of a lower inspection apparatus, namely an SEM or FIB, is described. However, the technique is by no means limited to the above-mentioned technique, and a technique in which marking is carried out in an SEM and the defect is observed/analyzed by means of another SEM or FIB may be employed.

Furthermore, it is desirable that the control unit of the SEM or FIB has a program for carrying out automatic positioning of the view in the field by means of the sample stage and image shift deflector based on the defect position information obtained from the SEM defect inspection apparatus as well as a program for carrying out specification of the target defect based on the mark that is located in the field of view or near the field of view and is prepared in the SEM defect inspection apparatus.

Next, it is desirable that the SEM defect inspection apparatus has a program for automatically preparing a mark that is used for specifying the defect position, that has been specified by means of an image comparison apparatus, by means of an SEM or FIB.

In defect/foreign-particle analysis by means of a charged particle beam inspection apparatus, FIB, SEM, and TEM, the position information of the electrical defect obtained by means of the charged particle beam inspection apparatus, in which it is difficult to find out an electrical defect by means of other apparatus, is transmitted easily and correctly to other different apparatus because marking is carried out in the inspection apparatus. As a result, analysis accuracy is improved and the analysis time is shortened.

What is claimed is:

1. A charged particle beam apparatus system comprising a circuit pattern inspection apparatus that irradiates a charged particle beam on a plurality of areas of a circuit pattern, detects secondary charged particles generated from the circuit pattern to form images of the irradiated areas, and compares the images of the plurality of areas to thereby detect a defect or a foreign-particle in the circuit, and a charged particle beam apparatus that is used for observation or analysis of the defect specified by means of the pattern inspection apparatus, wherein charging is formed by means of irradiation of the charged particle beam or carbon-base deposit is formed on the irradiated area as the result of interaction between the charged particle beam and gas that is remaining in the circuit pattern inspection apparatus or generated from the sample, and the charging or deposit is used as a mark in the charged particle beam apparatus, wherein a gas introduction mechanism for spraying gas onto the circuit pattern is provided in the pattern inspection apparatus, wherein a cooling unit for cooling the circuit pattern is provided, and wherein the charged particle beam is irradiated onto a portion including the defect or the foreign-particle in the circuit such that a temperature of the portion is kept at a temperature higher than the environmental temperature.

2. A charged particle beam apparatus system comprising a circuit pattern inspection apparatus that irradiates a charged particle beam on a plurality of areas of a circuit pattern, detects secondary charged particles generated from the circuit pattern to form images of the irradiated areas, and compares the images of the plurality of areas to thereby detect a defect or a foreign-particle in the circuit, and a charged particle beam apparatus that is used for observation or analysis of the defect specified by means of the pattern inspection apparatus, wherein charging is formed by means of irradiation of the charged particle beam or carbon-base deposit is formed on the irradiated area as the result of interaction between the charged particle beam and gas that is remaining in the circuit pattern inspection apparatus or generated from the sample, and the charging or deposit is used as a mark in the charged particle beam apparatus, wherein the charged particle beam is irradiated onto the circuit pattern including the defect or the foreign-particle such that a temperature of the circuit pattern is kept at a temperature higher than the environmental temperature so as to cause charging on the circuit pattern in the pattern inspection apparatus and to form a mark on the periphery of the defect or the foreign-particle in the circuit.

3. A method for forming an image in which a charged particle beam is scanned on a sample to form an image of the scanned area, wherein the charged particle beam is irradiated selectively onto a specified portion including the defect or the foreign-particle in a circuit such that a temperature of the portion is kept at a temperature higher than the environmental temperature and the charging formed by the irradiation is used as a mark in the image so as to cause charging on the specified portion that is different from charging of the scanned area other than the specified portion.

4. An inspection method in which a charged particle beam is scanned onto a semiconductor device in a first charged particle beam apparatus to form an image of the scanned area, the charged particle beam is irradiated selectively onto a specified portion so as to cause charging on the specified portion including a defect or a foreign-particle such that a temperature of the portion is kept at a temperature higher than the environmental temperature that is different from charging of the scanned area other than the specified portion, the semiconductor device is transferred to a second charged particle beam apparatus keeping the charging condition, and the charged particle beam is irradiated onto the portion to be inspected that is specified by the charging for inspection of the portion.

5. A charged particle beam apparatus system comprising a circuit pattern inspection apparatus that irradiates a charged particle beam on a plurality of areas of a circuit pattern, detects secondary charged particles generated from the circuit pattern to form images of the irradiated areas, and compares the formed images of the plurality of areas to thereby detect a defect or a foreign-particle in the circuit, and comprising a charged particle beam apparatus that irradiates a charged particle beam onto the defect, the area including foreign-particle, or the peripheral area that has been detected by means of the circuit pattern inspection apparatus and detects charged particles released from the defect or the area including foreign-particle to thereby form an image of the defect or the area including foreign-particle, and wherein the charged particle beam is irradiated onto a portion including the defect or the foreign-particle such that a temperature of the portion is kept at a temperature higher than the environmental temperature, wherein a mark for specifying the foreign-particle or defect detected by means of the circuit pattern inspection apparatus is formed by means of irradiation of the charged particle beam so that charging on the mark is different from that on the area other than the mark, and the field of view is matched for forming an image of the defect or the area including foreign-particle in the charged particle beam apparatus based on the formed mark.

6. A circuit pattern inspection apparatus that irradiates a charged particle beam onto a plurality of areas of a circuit pattern and detects secondary charged particles released from the circuit pattern to form an image of the irradiated areas, and compares a plurality of formed images to detect a defect or a foreign-particle of the circuit, wherein a mark that can be used for specifying the detected defect or foreign-particle of the circuit is formed in the form of charging by means of irradiation of the charged particle beam, and wherein the charged particle beam is irradiated onto a portion including the defect or the foreign-particle such that a temperature of the portion is kept at a temperature higher than the environmental temperature.

* * * * *